United States Patent [19]

Döscher et al.

[11] Patent Number: 4,950,813
[45] Date of Patent: Aug. 21, 1990

[54] PREPARATION OF SUBSTITUTED BENZOTRICHLORIDES

[75] Inventors: Frank Döscher, Langenfeld; Karl-Erwin Schnalke, Leverkusen, both of Fed. Rep. of Germany

[73] Assignee: Bayer Aktiengesellschaft, Leverkusen, Fed. Rep. of Germany

[21] Appl. No.: 238,073

[22] Filed: Aug. 30, 1988

[30] Foreign Application Priority Data

Sep. 11, 1987 [DE] Fed. Rep. of Germany ....... 3730476

[51] Int. Cl.⁵ .............................................. C07C 19/08
[52] U.S. Cl. ..................................... 560/127; 562/859
[58] Field of Search ......................... 560/127; 562/859

[56] References Cited

U.S. PATENT DOCUMENTS 2,211,467 8/1940 Kimball et al. ................. 260/544 D
4,318,866 3/1982 Robey et al. .................... 260/544 D

FOREIGN PATENT DOCUMENTS 3220729 8/1983 Fed. Rep. of Germany ... 260/544 D
898307 6/1962 United Kingdom .

Primary Examiner—Paul J. Killos
Attorney, Agent, or Firm—Sprung Horn Kramer & Woods

[57] ABSTRACT

A process for chlorinating a compound of the formula

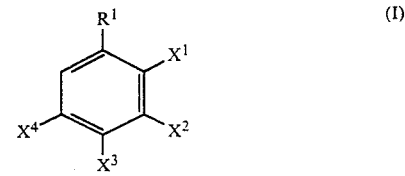

in which
  $R^1$ is a $C_1$-alkyl radical, $C_1$-alkoxy radical or $C_1$-thioalkyl radical, and
  $X^1$, $X^2$, $X^3$ and $X^4$ are identical or different hydrogen or halogen, and
  $X^3$ may alternatively be

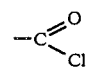

or —NCO, comprising, in an initial phase, dissolving a chlorination catalyst in the compound to be chlorinated, continuously metering this solution together with chlorine into a reaction vessel containing the compound to be chlorinated, and, after the initial phase, removing partially or fully chlorinated compounds from the reaction vessel, dissolving fresh chlorination catalyst in the removed compounds, and feeding this catalyst solution, together with chlorine, to the reaction vessel.

2 Claims, No Drawings

PREPARATION OF SUBSTITUTED BENZOTRICHLORIDES

The invention relates to a process for the preparation of substituted benzotrichlorides, in particular of 2,4-dichloro-5-fluorobenzotrichloride, which, via hydrolysis, results in the corresponding benzoyl chloride and thus represents an important starting product for highly powerful antibacterial agents, such as ciprofloxacin.

Benzotrichlorides are important intermediates, since they may be converted into the corresponding benzal chlorides or benzoyl chlorides by partial or complete hydrolysis of the trichloromethyl group, or into benzotrifluorides by fluorination.

The starting compounds in the process according to the invention for the preparation of the substituted benzotrichlorides correspond to the formula (I)

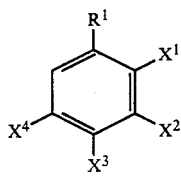

in which
$R^1$ stands for $C_1$-alkyl, $C_1$-alkoxy or $C_1$-thioalkyl and
$X^1, X^2, X^3$ and $X^4$ are identical or different and denote hydrogen, halogen, —COCl or —NCO.

As is generally known, chlorination of the methyl group follows a free-radical mechanism. For this, it is necessary to employ free-radical generators, for example organic peroxides, UV light or high temperatures (>180° C.). With reference to application and choice of the half-life period, the use of organic peroxides is advantageous as far as process engineering is concerned. It is disadvantageous that some peroxides, such as, for example, dibenzoyl peroxide, are supplied as an aqueous paste (dephlegmation). Chlorination of the methyl group to give the desired compound can generally only be carried out when the peroxides are metered continuously into the batch in anhydrous dissolved form. Good solvents for the organic peroxides are methylene chloride or carbon tetrachloride, which, however, at the temperatures of chlorination (>100° C.) evaporate immediately and thus greatly contaminate the reaction exhaust gas and the waste water.

The invention relates both to a batch process and a continuous process for the preparation of substituted benzotrichlorides by chlorination of compounds of the formula (I)

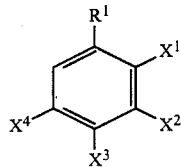

in which
$R^1$ stands for a $C^1$-alkyl radical, $C^1$-alkoxy radical or $C^1$-thioalkyl radical,
$X^1, X^2, X^3$ and $X^4$ are identical or different and denote hydrogen and halogen and
$X^3$, moreover, may be

or —NCO,
characterized in that, in an initial phase, chlorination catalysts are dissolved in compounds of the formula I, this solution, together with chlorine, is metered into a reaction vessel into which compounds of the formula (I) have been initially introduced for chlorination, and the chlorination is carried out continuously, and in that, after the initial phase, partially or fully chlorinated compounds derived from the formula (I) are removed from the reaction vessel, fresh chlorination catalyst is dissolved in these compounds, and this catalyst solution, together with chlorine, is fed to the reaction vessel.

For example, a procedure is carried out in which 600 to 1,000 kg of 2,4-dibromo-5-fluorotoluene are initially introduced into a suitable enamel kettle and heated to 100 to 150° C., 60 to 100 kg of 2,4-dibromo-5-fluorotoluene—later in the procedure 60 to 100 kg of the partially chlorinated substance—are initially introduced into a 100 l enamel kettle, 2 to 6 kg of a peroxide-type catalyst are added and dissolved at 30° to 60° C., the catalyst solution is metered into the chlorination batch at a rate of approximately 3 to 6 l/h, the batch is converted into the chlorination product 2,4-dichloro-5-fluorobenzotrichloride, and the latter is converted into 2,4-dichloro-5-fluorobenzoyl chloride, if appropriate by hydrolysis.

The catalyst used is preferably di-lauroyl peroxide. It is however also possible to use other peroxide catalysts. Decisive for the choice is their solubility in the partially chlorinated reaction mixture and their half-life period, which depends on the chlorination temperature. Suitable are, for example, dioctanoyl peroxide, bis-(2-methylbenzoyl) peroxide and t-butyl peroxypivaloate.

Advantages

1. No use of aqueous catalyst substances, hence no need for drying.
2. No use of low-boiling chlorinated hydrocarbons, such as carbon tetrachloride and methylene chloride, thus no need for laborious separation from the process waste water and the exhaust air.
3. Easier purification possible for the recovered bromine since the possible formation of azeotropes with the solvent is avoided.
4. Preferred compounds used for the process according to the invention are those of the formula (I) in which $X^4$ denotes fluorine, and $X^1$ and $X^3$ denote Cl, Br, NCO or

Particularly preferred compounds used for the process according to the invention are those of the formula (I) in which $R^1$ denotes $C_1$-alkyl.

In particular, compounds of the formula (I) in which $R^1$ denotes methyl, $X^4$ denotes fluorine, and $X^1$ and $X^3$ both denote bromine are used for the process.

EXAMPLE 1

600 kg of the compound to be chlorinated are initially introduced into a 500 l enamel kettle and heated to 130° C.

60 kg (or, later in the procedure, 60kg of the partially chlorinated substance) are initially introduced into a 100 l enamel kettle; 3 kg of di-lauroyl peroxide are added and dissolved at 30° to 40° C. This catalyst solution is metered into the chlorination batch at a rate of approximately 3 l/h. During a chlorination period of approximately 50 h, approximately 1,000 kg of chlorine and 12 to 15 kg of peroxide catalyst are consumed. According to GC, the content of the crude product (715 kg) is approximately 98%.

In accordance with this process, approximately 20 kg of di-lauroyl peroxide are required per ton of 2,4-dibromo-5-fluorotoluene (based on: 0.5 m³ kettle); further auxiliary substances are not required.

EXAMPLE 2

618 g of 2,4-dibromo-5-fluorotoluene, 6.9 g of dilauroyl peroxide (~0.5 g/h), 13 hours reaction time with passing in chlorine in excess, 2100 g of final product 2,4-dichloro-5-fluorobenzotrichloride, 97.6 % yield.

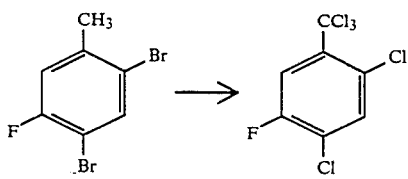

EXAMPLE 3

387 g of toluene, 15 g of di-lauroyl peroxide (~1.0 g/h), 14 h reaction time with passing in chlorine in excess, 754 g of final product benzotrichloride, 94.7% yield.

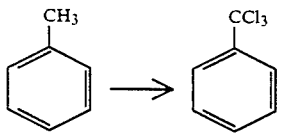

EXAMPLE 4

900 g of p-methoxybenzoyl chloride, 15 g of dilauroyl peroxide (~0.75 g/h), 20 hours reaction time with passing in chlorine in excess, 1373 g of final product trichloromethoxybenzoyl chloride, 93 % yield.

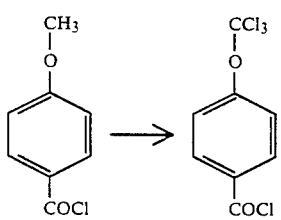

EXAMPLE 5

4275 g of 4-methylbenzoyl chloride, 44 g of dilauroyl peroxide (~1 g/h), 40 hours reaction time with passing in chlorine in excess, 6647 g of final product 4-trichloromethylbenzoyl chloride, 90% yield.

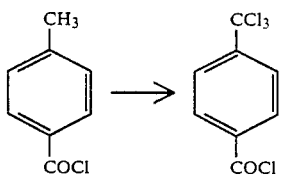

EXAMPLE 6

1200 g of p-tolylisocyanate, 12 g of di-lauroyl peroxide (~1 g/h), 12 hours reaction time with passing in chlorine in excess, 1970 g of final product (92%)(p-trichloromethyl)phenyl isocyanate, 95% yield.

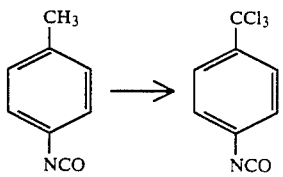

EXAMPLE 7

2500 g of o-xylene (96%), 30 g of di-lauroyl peroxide (~1 g/h), 30 hours reaction time with passing chlorine in excess, 6400 g of final product 46%) (o-trichloromethylbenzal chloride)

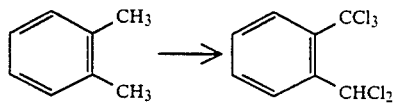

Following the same method 2-chloro-4-methylphenyl isocyanate can also be chlorinated to 2-chloro-4-trichloromethylphenyl isocyanate.

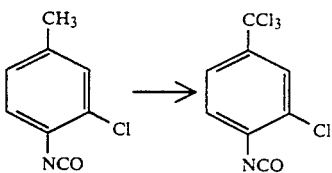

It will be appreciated that the instant specification and claims are set forth by way of illustration and not limitation, and that various modifications and changes may be made without departing from the spirit and scope of the present invention.

What is claimed is:

1. A process for chlorinating 2,4-dichloro-5-fluorotoluene comprising initially introducing 600 to 1,000 parts by weight of 2,4- dibromo-5-fluorotoluene into a first enamel kettle and heating to 100° to 150° C., introducing 60 to 100 parts by weight of partially chlorinated 2,4-dibromo-5-fluorotoluene into a second enamel kettle, dissolving 2 to 6 parts by weight of a peroxide catalyst at 30° to 60° C. in the second kettle, and metering the catalyst solution from the second kettle into the first kettle at a rate of approximately 3 to 6 l/h along the chlorine thereby to form 2,4-dichloro-5-fluorobenzo-trichloride.

2. A process according to claim 1, wherein the catalyst is di-lauroyl peroxide.